United States Patent [19]
Chiang et al.

[11] Patent Number: 5,770,219
[45] Date of Patent: *Jun. 23, 1998

[54] SOLID MATRIX SYSTEM FOR TRANSDERMAL DRUG DELIVERY

[75] Inventors: Chia-Ming Chiang, Foster City; Renee Ann Tenzel, Mountain View, both of Calif.

[73] Assignee: Cygnus Inc., Redwood City, Calif.

[ * ] Notice: The term of this patent shall not extend beyond the expiration date of Pat. No. 5,252,334.

[21] Appl. No.: 311,914

[22] Filed: Sep. 26, 1994

Related U.S. Application Data

[60] Continuation of Ser. No. 88,793, Jul. 8, 1993, abandoned, which is a division of Ser. No. 857,094, Mar. 20, 1992, Pat. No. 5,252,334, which is a continuation of Ser. No. 405,630, Sep. 8, 1989, abandoned.

[51] Int. Cl.⁶ .................................................. A61F 13/02
[52] U.S. Cl. .......................................... 424/448; 424/448
[58] Field of Search ..................................... 424/448, 449

[56] References Cited

U.S. PATENT DOCUMENTS

| | | | |
|---|---|---|---|
| 3,426,754 | 2/1969 | Bierenbaum et al. | 604/307 |
| 3,632,740 | 1/1972 | Robinson et al. | 424/448 |
| 3,645,835 | 2/1972 | Hodgson | 428/195 |
| 3,685,734 | 8/1972 | Paciorek et al. | 239/56 |
| 3,725,122 | 4/1973 | Reinhard et al. | 428/355 CN |

(List continued on next page.)

FOREIGN PATENT DOCUMENTS

| | | |
|---|---|---|
| 1 255 592 | 6/1989 | Canada . |
| 1312800 | 1/1993 | Canada . |
| 0 156 080 | 10/1985 | European Pat. Off. . |
| 0 209 975 | 1/1987 | European Pat. Off. . |
| 0 223 524 | 5/1987 | European Pat. Off. . |
| 0 252 712 | 1/1988 | European Pat. Off. . |
| 275716 | 7/1988 | European Pat. Off. . |
| 0 328 806 | 8/1989 | European Pat. Off. . |
| 0379045 | 7/1990 | European Pat. Off. . |
| 0186019 | 10/1993 | European Pat. Off. . |
| 57-142258 | 9/1982 | Japan . |
| 57-179271 | 11/1982 | Japan . |
| 60-66759 | 4/1985 | Japan . |
| 60-123417 | 7/1985 | Japan . |
| 7-101853 | 4/1995 | Japan . |
| 153637 | 11/1980 | Norway . |
| 171950 | 3/1986 | Norway . |
| 2 086 224 | 5/1982 | United Kingdom . |
| 86/00814 | 2/1986 | WIPO . |
| 87/03477 | 6/1987 | WIPO . |
| 89/07951 | 9/1989 | WIPO . |
| 90/07940 | 7/1990 | WIPO . |
| 93/20165 | 10/1993 | WIPO . |
| 97/23205 | 7/1997 | WIPO . |

OTHER PUBLICATIONS

Translation of Japanese laid–open patent publ. No. 7–101853, laid–open publ. date Apr. 18, 1995.

Abstract of Japanese Patent No. 6–279266 from Derwent World Patent Index, Oct. 4, 1994.

Abstract of Japanese Patent No. 4–368322 from Derwent World Patent Index, Jun. 12, 1991.

Megrab et al. "Oestradiol permeation through human skin and silastic membrane: effects of propylene glycol and supersaturation" J. Controlled Release (1995) 36:277–294.

(List continued on next page.)

*Primary Examiner*—D. Gabrielle Phelan
*Attorney, Agent, or Firm*—Morrison & Foerster LLP

[57] ABSTRACT

A matrix for containing drugs for transdermal delivery systems is disclosed. The matrix, formed of a skin-adhesive acrylate copolymer, attains high rates of drug delivery without the addition of drug delivery rate enhancers. In preferred embodiments the matrix is used to administer steroids, in particular estradiol. Water-soluble polymers may be added as well.

20 Claims, 2 Drawing Sheets

U.S. PATENT DOCUMENTS

| | | | |
|---|---|---|---|
| 3,769,071 | 10/1973 | Trancik | 424/448 |
| 3,849,238 | 11/1974 | Gould et al. | 602/46 |
| 3,896,789 | 7/1975 | Trancik | 604/307 |
| 4,181,752 | 1/1980 | Martens et al. | 427/516 |
| 4,331,651 | 5/1982 | Reul et al. | 424/434 |
| 4,379,454 | 4/1983 | Campbell et al. | 424/448 |
| 4,421,737 | 12/1983 | Ito et al. | 424/449 |
| 4,438,139 | 3/1984 | Keith et al. | 514/177 |
| 4,452,845 | 6/1984 | Lloyd et al. | 602/52 |
| 4,460,372 | 7/1984 | Campbell et al. | 424/449 |
| 4,510,197 | 4/1985 | Shah | 428/220 |
| 4,552,751 | 11/1985 | Inaba et al. | 424/449 |
| 4,560,553 | 12/1985 | Zupan | 514/11 |
| 4,608,249 | 8/1986 | Otsuka et al. | 424/28 |
| 4,655,768 | 4/1987 | Marecki et al. | 424/448 |
| 4,668,232 | 5/1987 | Cordes et al. | 424/448 |
| 4,687,481 | 8/1987 | Nuwayser | 424/449 |
| 4,695,465 | 9/1987 | Kigasawa et al. | 424/449 |
| 4,781,926 | 11/1988 | Hyon et al. | 424/486 |
| 4,818,540 | 4/1989 | Chien et al. | 424/448 |
| 4,883,669 | 11/1989 | Chien et al. | 424/448 |
| 4,906,169 | 3/1990 | Chien et al. | 424/448 |
| 4,906,475 | 3/1990 | Kim | 424/449 |
| 4,971,799 | 11/1990 | Nakagawa et al. | 424/448 |
| 4,994,267 | 2/1991 | Sablotsky | 424/78 |
| 5,023,084 | 6/1991 | Chien et al. | 424/448 |
| 5,059,189 | 10/1991 | Cilento et al. | 604/307 |
| 5,069,909 | 12/1991 | Sharma | 424/449 |
| 5,145,682 | 9/1992 | Chien et al. | 424/448 |
| 5,152,997 | 10/1992 | Ebert et al. | 424/449 |
| 5,223,261 | 6/1993 | Nelson et al. | 424/443 |
| 5,252,334 | 10/1993 | Chiang et al. | 424/448 |
| 5,296,230 | 3/1994 | Chien et al. | 424/448 |
| 5,314,694 | 5/1994 | Gale et al. | 424/448 |
| 5,362,497 | 11/1994 | Yamada et al. | 424/449 |
| 5,376,377 | 12/1994 | Gale et al. | 424/448 |
| 5,422,119 | 6/1995 | Casper | 424/449 |
| 5,505,956 | 4/1996 | Kim et al. | 424/448 |
| 5,554,381 | 9/1996 | Roos et al. | 424/449 |
| 5,560,922 | 10/1996 | Chien et al. | 424/448 |

OTHER PUBLICATIONS

English Abstract of Japanese Laid–Open Patent Publication Number 57–075917. Laid–Open Publication Date: May 12, 1982.

English Abstract of Japanese Laid–Open Patent Publication Number 61–151122. Laid–Open Publication Date: Jul. 9, 1986.

Kligman et al., "Preparation of isolated sheets of human stratum corneum" *Arch. Dermatol.* (1963) 88:702–705.

Nitto Electric Industrial Co., Ltd., "Transdermal analgesic tapes" *Chemical Abstracts* (1985) 102:354 (Abstract 154817h).

Translation of Japanese Laid–Open Patent Publication Number 60–66759. Laid–Open Publication Date: Apr. 16, 1985.

Translation of Japanese Laid–Open Patent Publication Number 60–123417. Laid–Open Publication Date: Jul. 2, 1985.

Wolff, "In vitro models in the development of transdermal drug delivery systems and their practical relevance for in vivo transdermal absorption" *Transdermal Drug Delivery* Jaeger et al., eds., Neu–Ulm Conference (1986) pp. 68–76.

SOLID MATRIX SYSTEM FOR TRANSDERMAL DRUG DELIVERY

This application is a continuation of application Ser. No. 08/088,793, filed Jul. 8, 1993, now abandoned, which is a division of Ser. No. 07/857,094, filed Mar. 20, 1992, now U.S. Pat. No. 5,252,334, which is a continuation of Ser. No. 07/405,630, filed Sep. 8, 1989, now abandoned.

DESCRIPTION

1. Technical Field

This invention relates generally to the transdermal administration of drugs. More particularly, it concerns a configuration for transdermal drug delivery devices which enables the administration of effective levels of drugs without the necessity for coadministration with skin penetration rate enhancers.

2. Background

Transdermal delivery of drugs, that is, delivery of drugs through the skin, provides many advantages. The method is a comfortable, convenient, and noninvasive way of administering drugs. Many of the variables and side effects associated with oral administration are eliminated. Since the early 1970s, there has been substantial effort spent on developing particular systems for effectively delivering drugs in a transdermal mode. A variety of devices containing, at minimum, a drug reservoir and a backing, and optionally containing other layers, such as an adhesive layer for adhering the device to the patient, a drug release rate controlling layer for moderating delivery rate, and the like, have been constructed. With certain drugs, in particular scopolamine and nitroglycerine, it is feasible to construct a transdermal drug delivery device which will achieve therapeutically effective levels of the drug in the patient. Commercial products have been introduced to deliver these two materials. However, one of the key problems with transdermal administration of many other drugs has been the low penetration or permeation rate of drug through the skin of the patient. The research over the past two decades has identified various skin permeation enhancers. These materials increase the rate of penetration of drugs across the skin.

Typical enhancers in the art include ethanol, glycerol monolaurate, PGML (polyethylene glycol monolaurate), dimethylsulfoxide, and the like. Many highly attractive drugs, such as estradiol, progestins and the like are commonly formulated with enhancers for transdermal delivery.

The use of permeation enhancers is not without its drawbacks. For one, the permeation enhancer typically is coadministered with the desired drug. That is, the permeation enhancer passes through the patient's skin at the same time the drug does. Depending upon the exact nature of the permeation enhancer, this can lead to side effects related directly to the permeation enhancers.

Another disadvantage is that the enhancers are often organic solvents, which can in some cases react with and alter the character of the drug being delivered. In addition, the enhancers can interact with the patient's skin, in some cases causing irritation and the like. Moreover, enhancers can interfere with the mechanical properties of the devices, such as interfering with the effectiveness of adhesive layers and the like.

The present invention provides drug-matrix constructions which, when contacted with patient skin, allow high rates of delivery of drug without the necessity of added permeation enhancers previously required to reach therapeutic blood levels.

DISCLOSURE OF THE INVENTION

It has now been found that the necessity for incorporating permeation enhancers into drug delivery systems can be reduced or eliminated by incorporating the drug in a matrix comprising a vinyl acetate-acrylate copolymer and delivering the drug to the patient from this matrix.

This invention can take the form of a transdermal drug delivery device for administering a drug to a predetermined area of skin or mucosa of a patient. This device can be made up as a laminated composite that includes (a) a backing layer that is substantially impermeable to the drug and defines the face surface of the composite, and (b) a matrix layer made up of a pressure-sensitive vinyl acetate-acrylate copolymer forming the bottom surface of the device and which serves to adhere the device to the skin or mucosa of the patient, said layer having the drug dispersed therein.

Such a device can give rise to high rates of drug delivery with little or no added permeation enhancer present.

The invention can also take the form of the matrix itself.

In another aspect, the invention provides a method of transdermal drug delivery employing the matrix and device of this invention.

In preferred embodiments, the matrix of this device can additionally contain hydrophilic polymers such as the water-soluble polymers, for example, polyvinyl alcohol or polyvinyl pyrrolidone.

BRIEF DESCRIPTION OF THE DRAWINGS

This invention will be described with reference being made to the accompanying drawings, in which.

MODES FOR CARRYING OUT THE INVENTION

Definitions

Figure 1:
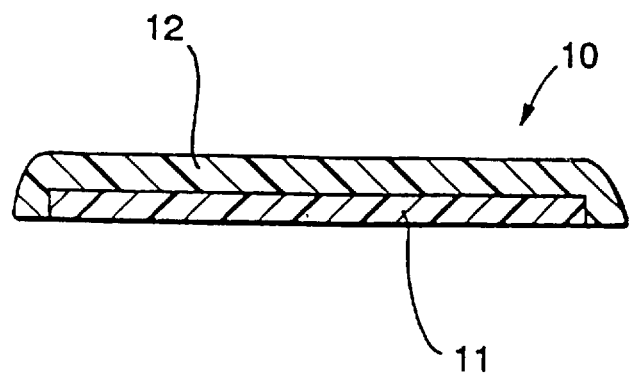
FIG. 1 is a not-to-scale cross-sectional view of one form of drug delivery device constructed using the teachings of this invention.

In this specification and claims certain terms will be used which have defined meanings.

By "transdermal" delivery is intended both transdermal (or "percutaneous") and transmucosal administration, i.e., delivery by passage of a drug through the skin or mucosal tissue and into the bloodstream.

"Carriers" or "vehicles" as used herein refer to carrier materials suitable for transdermal drug administration, and include any such materials known in the art, e.g., any liquid, gel, solvent, liquid diluent, solubilizer, or the like, which is nontoxic and which does not interact with other components of the composition or the skin in a deleterious manner. Examples of suitable carriers for use herein include water, mineral oil, silicone, liquid sugars, waxes, petroleum jelly, and a variety of other oils and polymeric materials. In addition, one or both of the components of the present enhancer composition may also serve as a carrier.

"Permeation enhancement" and "permeation enhancers" as used herein relate to the process and added materials which bring about an increase in the permeability of skin to a poorly skin permeating pharmacologically active agent, i.e., so as to increase the rate at which the drug permeates through the skin and enters the bloodstream. The enhanced permeation effected through the use of such enhancers is not required when the matrix compositions of the present invention are employed.

By the term "pharmacologically active agent" or "drug" as used herein is meant any chemical material or compound suitable for transdermal or transmucosal administration which induces a desired systemic effect. Such substances include the broad classes of compounds normally delivered through body surfaces and membranes, including skin. In general, this includes: anti-infectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers, beta-blockers such as pindolol, anti-arrhythmics, antihypertensives, diuretics, and vasodilators including general coronary, peripheral and cerebral; central nervous system stimulants; cough and cold preparations, including anti-histamine decongestants; hormones such as the estrogens estradiol and progesterone and other steroids, including corticosteroids; hypnotics; immunosuppressives; muscle relaxants; parasympatholytics; psychostimulants; sedatives; and tranquilizers.

Steroid drugs represent a preferred class of drugs for use in conjunction with the drug delivery device and matrix composition of the present invention. Steroid drugs have been difficult materials to administer transdermally, historically because of their generally poor (low) skin permeation properties. Historically, skin permeation enhancers have been used to achieve therapeutic blood-levels in patients. Thus this invention is of special advantage when used with such materials. Examples of steroid drugs useful herein include: progestogens such as norethindrone, norethindrone acetate, desogestrel, 3-keto desogestrel, gestadene and levonorgestrel; estrogens such as estradiol and its esters, e.g., estradiol valerate, cyprionate, decanoate and acetate, as well as ethinyl estradiol; androgens such as testosterone and its esters; and corticosteroids such as cortisone, hydrocortisone, and fluocinolone acetonide. In a particularly preferred embodiment, the devices and matrices of the invention include one or more estrogens, in particular estradiol, and may include one or more progestogens, as well.

By "therapeutically effective" amount of a pharmacologically active agent is meant a nontoxic but sufficient amount of a compound to provide the desired therapeutic effect.

"Water-soluble polymer" means a hydrophilic polymer having a solubility in water of greater than 0.1% by weight.

The Matrix Material

A key element of this invention is the use of a matrix which permits high delivery rates for drugs without the use of added skin penetration rate enhancers.

It has been found that matrices made from acetate-acrylate copolymer give rise to unexpectedly high rates of drug delivery. These acetate-acrylate copolymer materials are available commercially. For example, Monsanto Chemical Company distributes a family, of vinyl acetate-acrylate copolymer resin solutions under the trademarks GELVA® 737 and GELVA® 788 and Morton Thiokol, Inc. distributes acrylate copolymers under the trademarks Morstik 207A and Morstik 607.

These acrylate copolymer materials can be used separately or in mixtures. Several specific materials which have given rise to superior results are the Morstik 607 material, the GELVA® materials, which are believed to be based on 2-ethylhexyl acrylate, and mixtures of from about 20:1 to about 1:1 parts GELVA® 737 and GELVA® 788 (ratios given as weight ratios of GELVA® 737 to GELVA® 788). All of these materials are solvent based but form films following casting and removal of the solvent. The term "solid" is used broadly since the "solid" product is generally a tacky, amorphous (i.e. pressure sensitive adhesive) non-flowing material.

These materials are typically available as solutions in organic solvents such as toluene, ethanol, isopropanol, ethyl acetate and the like. These solvents are substantially eliminated from the matrix during fabrication.

These copolymers have the property of being high tack pressure sensitive adhesive when dried and/or cured. Thus, the matrices formed from these materials can adhere directly to the patient's skin without the need for additional separate adhesives.

Devices and Device Fabrication

The devices of this invention include a solid body of the matrix-forming copolymer material throughout which the drug is incorporated. This incorporation can be carried out by simply dissolving or otherwise finely dispersing the drug in a solution of the matrix material to yield a solution or slurry, casting the slurry or solution that contains the drug matrix and then evaporating the volatile solvents to give a solid matrix with drug incorporated therein.

The incorporating can be carried out with conventional polymer solution-handling equipment such as mixers, mills or the like, and can be completed in from a few seconds to a few hours, depending upon mixing conditions. Generally, it is continued until a uniform solution or homogeneous dispersion is attained.

Although not known with certainty and without intention to be bound to any particular mode of operation, it is believed that the high drug flux rate obtained using the matrices of this invention may in part result from the fact that the drug is contacted with the matrix-forming solution prior to solidification. This contact may result in at least partially dissolving the drug in the matrix phase, changing the drug's crystalline form to a more polymorphic structure, or forming a microdispersion of the drug in the matrix polymer.

The casting can be carried out using manual casting machines or doctor blades or the like or can be carried out with commercial film casting equipment for large scale production.

The thickness of the matrix can vary from 10 micrometers to about 250 micrometers. Preferred thicknesses are from 15 to 100 micrometers. These relatively thin layer thicknesses are of advantage in assuring the completeness of the subsequent solvent removal step.

The solvent removal should be thorough and is carried out using heat, air flow and/or a vacuum. Temperatures should be held below temperatures at which significant degradation of drug occurs and typically range from room temperature (approximately 20° C. to 25° C.) to about 100° C. although higher temperatures can be used if the nature of the drug permits.

The solvent removal should be carried out completely until no substantial solvent remains, for example until the solvent level is less than 5%, preferably less than 1% by weight.

As shown in FIG. 1, the device 10 of this invention includes a matrix 11 having drug dispersed therethrough and can in addition include a backing layer 12. Backing 12 is provided to contain the drug and prevent its loss.

The matrices and devices of this invention can be of any size suitable for transdermal drug delivery. This encompasses an area of from about 0.5 cm$^2$ to about 100 cm$^2$.

Backing 12 is generally a water-occlusive layer preferably made of a sheet or film of a preferably flexible elastomeric material that is substantially impermeable to the selected drug. The layer is preferably on the order of 1 micrometer to 100 micrometers in thickness, and may or may not contain pigment. The layer is preferably of a material that permits the device to mimic the contours of the skin and be worn comfortably on areas of skin, such as at joints or other points of flexure, that are normally subjected to mechanical strain with little or no likelihood of the device disengaging from the skin due to differences in the flexibility or resiliency of the skin and the device. Elastomeric materials generally present these desired properties. Examples of elastomeric polymers that are useful for making layer 11 are polyether block amide copolymers (e.g., PEBAX copolymers), polyethylene methyl methacrylate block copolymers (EMA) such as NUKRELL polymers, polyurethanes such as PELLATHANE or ESTANE polymers, silicone elastomers, polyester block copolymers that are composed of hard and soft segments (e.g., HYTREL polymers), rubber-based polyisobutylene, styrene, and styrene-butadiene and styrene-isoprene copolymers. Polymers that are flexible but not elastomeric include polyethylene, polypropylene, polyesters, e.g., polyester terephthalate (PET), which may be in the form of films or laminates. The preferred polymer used for the backing will depend on the material or drug incorporated into the device and on the nature of any vehicles, solubilizers, or the like that are used.

Figure 2:
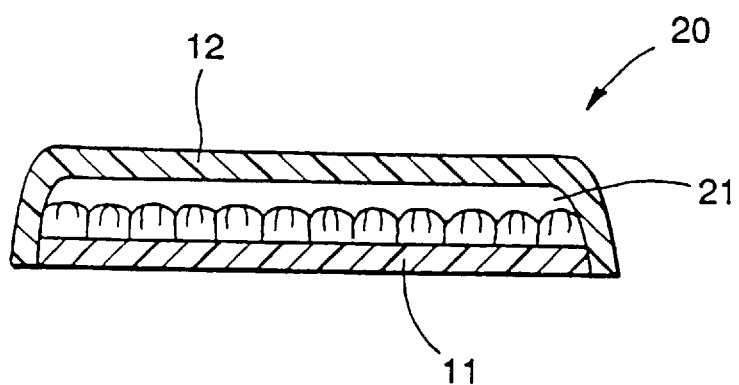
FIG. 2 is a not-to-scale cross-sectional view of a second form of drug delivery device constructed using the teachings of this invention.

In a second embodiment, as shown in FIG. 2, a device 20 can include in addition to the matrix 11 and backing 12 as just set forth a drug reservoir 21. This reservoir can be a void in which additional drug and (as needed) carrier are lodged or can contain a porous substrate such as a porous polymer or sponge which holds and easily delivers drug to the matrix 11 for continuous administration to the patient.

As previously pointed out, the devices of the invention can advantageously contain added water-soluble water-absorptive polymer. These materials are added solely to improve long-term wearing properties by absorbing moisture from the wearer's skin and are not seen to modify or enhance the rate of drug delivery.

The water-soluble polymers that can be used in the invention include, for example, polyvinyl alcohol, gelatine, polyacrylic acid, sodium polyacrylate, methylcellulose, carboxymethylcellulose, polyvinylpyrrolidone, gum acacia, gum tragacanth, carrageenan, gum guar and the like gums and dextrans. They also include suitable cross-linked reaction products of these materials which may offer improved cohesion. These water-soluble polymers can be used either singly or in combinations of two or more. These water-soluble polymers can be of molecular weights varying from as low as 10,000 to several million (3,000,000). Polyvinyl alcohol and polyvinyl pyrollidone, two preferred polymers, are commercially available in sizes throughout the range.

Device Composition

The devices of this invention have a matrix composed of acrylate copolymer and drug. The matrix may also include a water-soluble polymer.

The matrix may, in addition, include one or more selected carriers or excipients, and various agents and ingredients commonly employed in dermatological ointments and lotions. For examples, fragrances, opacifiers, preservatives, antioxidants, gelling agents, perfumes, thickening agents, stabilizers, surfactants, emollients, coloring agents, and the like may be present.

The relative amounts of the components in these compositions can vary a great deal. For example, the amount of drug or drugs present in the composition will depend on a variety of factors, including the disease to be treated, the nature and activity of the drug, the desired effect, possible adverse reactions, the ability and speed of the drug to reach its intended target, and other factors within the particular knowledge of the patient and physician.

In typical embodiments, the matrix will contain from about 0.5% up to about 25% by weight (based on the total matrix weight) drug; for example, 1 to 10% by weight estrogen (estradiol) and 1 to 15% by weight progestogen, (norethindrone acetate) will be present in a preferred postmenopausal syndrome or contraceptive patch, and 1 to 15% by weight estradiol will be present in a preferred patch releasing only estrogen.

The matrix may be formulated so that the selected drug is contained therein below saturation, at saturation, or in excess.

The amount of water-soluble polymer may range from 0% (in light of its optional character) to as much as 40% by weight. When water-soluble polymer is present, use levels of 2 to 30% by weight are preferred.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

Monolith matrix systems in accord with this invention and based on estradiol, norethindrone, norethindrone acetate, and levonorgesterol were prepared by the following procedures: The drug was mixed and sonicated with or without a known skin penetration enhancer (PGML) for 10 minutes. Typical polymer solvents, if present, included lower alcohols such as ethanol and isopropanol and lower alkanoic acid esters such as ethylacetate. (These solvent materials were later removed during drying.) Monsanto GELVA® 737 vinyl acetate acrylate copolymer resin pressure-sensitive adhesive solution was added to the drug-solvent mixture and rotated overnight. The drug-solvent-polymer mixture was then cast to about 100 micrometers thickness on a polyester film (#1022 release liner). The solvent in the polymer system was evaporated in a 75° C. forced air oven for 15 to 20 minutes. The resultant drug reservoir matrix was laminated with another polyester film (3M #1022). For comparison, similar compositions (with and without PGML) were prepared using Dow Corning silicone as the matrix polymer.

Modified Franz flow-through cells were used for in vitro penetration studies which were carried out to determine the efficiency of the present matrices at delivering drugs. One of the two polyester layers was peeled off of the drug matrix layer. The drug matrix layer was gently pressed onto the stratum corneum of human cadaver skin membrane. This skin membrane with the backing and matrix affixed thereto was then mounted between the two half-cells and fastened with a clamp. The receiver compartment was filled with 0.1% gentamycin in distilled, deionized water and the temperature was maintained at 32° C. Samples were taken at preset intervals and assayed by HPLC. The flux was calculated from the slope of the cumulative amounts of the drug in the receiver compartment versus time.

The fluxes of estradiol, norethindrone, norethindrone acetate and levonorgesterol through human cadaver skin are summarized in Table 1. The fluxes for all of the drugs tested (i.e., estradiol, norethindrone acetate, norethindrone and levonorgesterol) were not affected by incorporation of the enhancer (PGML) in the acrylate matrix. However, the fluxes of norethindrone and norethindrone acetate did increase significantly when PGML was used in the silicone matrix. More importantly, the fluxes of estradiol, norethindrone and levonorgesterol from acrylate copolymer systems without enhancers were all comparable to those with PGML in the silicon matrix system. Although the flux of norethindrone acetate from the acrylate copolymer matrix was low, it may be due to a higher solubility of norethindrone acetate in the acrylate copolymer system. Therefore, the low loading (1%) of norethindrone acetate may not have enabled a higher driving force for the diffusion. By this reasoning, the norethindrone flux could be increased by increasing the drug loading in the polymer matrix until maximum thermodynamic activity is reached. It is an advantage of the present invention that since no enhancer need be present, higher thermodynamic activity can be achieved with less drug.

TABLE 1

In Vitro Skin Fluxes of Estradiol
and Progestogens Through Human Cadaver Skin
From Polymer Matrix With or Without PGML

| Drug | System | Fluxes (mcg/cm$^2$hr) |
|---|---|---|
| Estradiol (E2) | E2/PGML/silicone (5:14:81, w/w) | 0.14 ± 0.05 |
| | E2/PGML/acrylate (1:14:85) | 0.17 ± 0.00 |
| | E2/acrylate (1:99) | 0.12 ± 0.00 |
| Norethindrone (N) | N/PGML/silicone (1:14:85, w/w) | 0.20 ± 0.02 |
| | N/silicone (1:99) | 0.07 ± 0.02 |
| | N/PGML/acrylate (1:14:85) | 0.26 ± 0.08 |
| | N/acrylate (1:99) | 0.24 ± 0.09 |
| Norethindrone acetate (NA) | NA/PGML/silicone (1:14:85, w/w) | 0.54 ± 0.10 |
| | NA/silicone (1:99) | 0.17 ± 0.00 |
| | NA/PGML/acrylate (1:14:85) | 0.06 ± 0.03 |
| | NA/acrylate | 0.05 ± 0.01 |
| Levonorgesterol (LG) | LG/PGML/silicone (1:14:85, w/w) | 0.09 ± 0.02 |
| | LG/PGML/acrylate (1:14:85) | 0.22 ± 0.02 |
| | LG/acrylate (1:99) | 0.17 ± 0.04 |

EXAMPLE 2

A series of monolith systems of norethindrone acetate was prepared by the following procedures. Norethindrone acetate was mixed and sonicated with solvents and with or without enhancers (PGML and dipropylene glycol monoethyl ether "Transcutanol" (TC)) for 10 minutes. A solution of acrylate copolymer pressure-sensitive adhesive was added to the drug-vehicle mixture and rotated overnight.

The drug-solvent-polymer mixture was then cast on a polyester film (3M #1022 release liner). The solvent in the polymer system was thoroughly evaporated in a 75° C. forced air oven for 15–20 minutes. The resultant drug reservoir polymer matrix was laminated with another polyester film (3M #1022).

The in vitro permeation studies and data analyses were the same as in Example 1. Again, the fluxes of norethindrone acetate without enhancers were comparable to those with enhancers in the polymer matrix (Table 2). The results also show that in the acrylate matrix, the fluxes of norethindrone acetate were essentially independent of the presence of enhancers. Acrylate matrices without enhancers gave fluxes which are comparable to fluxes possible in conventional silicone matrices only with added enhancers.

TABLE 2

In Vitro Skin Fluxes of Norethindrone Acetate
From Polymer Matrix With and Without Enhancers

| System | Fluxes (mcg/cm$^2$/hr) |
|---|---|
| NA/PGML/silicone (2/10/88, w/w) | 0.19 ± 0.03 |
| NA/TC:PGML/acrylate (4/10/86, w/w) | 0.18 ± 0.02 |
| NA/PGML/acrylate (4/10/86, w/w) | 0.14 ± 0.02 |
| NA/acrylate (4/96, w/w) | 0.15 ± 0.03 |

EXAMPLE 3

A series of prototype systems was made. The drug reservoir layers were prepared as described in Example 2. However, 20% PVP (BASF, K-30) was suspended with the drugs (E2 and NA) in the polymer solution (Morstik 607) with addition of isopropanol. The drugs, PVP, polymer and solvents were then rotated overnight and a homogeneous solution was obtained. A uniform drug reservoir matrix was then cast on a polyester film (3M #1022). The solvent in the system was evaporated in a 75° C. forced air oven for 30 minutes. After cooling, the reservoir layer was laminated with a layer of polyisobutylene to an elastomeric backing membrane (Bertek #438, #810, or 3M 166) or laminated directly to a second layer of 3M #1022 polyester.

The in vitro permeation studies and data analyses were the same as in Example 1. The results show that in acrylate systems, the fluxes of both estradiol and norethindrone acetate were high without. employing enhancers (Table 3). The fluxes of the drugs increased as the percentage of drug increased in these systems. The fluxes reached maximum when 4% estradiol and 10% norethindrone acetate were present in the drug matrices. The flux of 2% estradiol in the system was 0.25 mcg/cm$^2$/hr, which is comparable to the commercial estrogen patches which include permeation enhancers. The flux of 10% norethindrone acetate reached 0.76 mcg/cm$^2$/hr, which indicates that effective levels of progestogens can be delivered from the system as well. The fluxes were comparable whether the backing material used was an occlusive polyester film or combined layers of PIB and an occlusive elastomeric layer.

TABLE 3

In Vitro Skin Fluxes of Estradiol and Norethindrone Acetate from
Acrylate Matrix Systems with Polyvinylpyrrolidone Incorporated

| System | | Fluxes (mcg/cm$^2$/hr) | |
|---|---|---|---|
| Drug Reservoir | Backing Layer | Estradiol | Norethindrone |
| E2/NA/PVP/acrylate | Polyester | 0.25 ± 0.03 | 0.38 ± 0.06 |

TABLE 3-continued

In Vitro Skin Fluxes of Estradiol and Norethindrone Acetate from
Acrylate Matrix Systems with Polyvinylpyrrolidone Incorporated

| System | | Fluxes (mcg/cm$^2$/hr) | |
|---|---|---|---|
| Drug Reservoir | Backing Layer | Estradiol | Norethindrone |
| (2/5/20/73, w/w) E2/NA/PVP/acrylate | PIB & 3M 166 | 0.28 ± 0.04 | 0.40 ± 0.04 |
| (2/5/20/73, w/w) E2/NA/PVP/acrylate | PIB & Bertek 428 | 0.27 ± 0.01 | 0.39 ± 0.00 |
| (2/5/20/73, w/w) E2/NA/PVP/acrylate | Polyester | 0.50 ± 0.13 | 0.76 ± 0.17 |
| (4/10/20/66, w/w) E2/NA/PVP/acrylate | PIB & 3M 166 | 0.43 ± 0.05 | 0.64 ± 0.05 |
| (4/10/20/66, w/w) E2/NA/PVP/acrylate | PIB & Bertek 810 | 0.39 ± 0.07 | 0.58 ± 0.11 |

EXAMPLE 4

Figure 3:
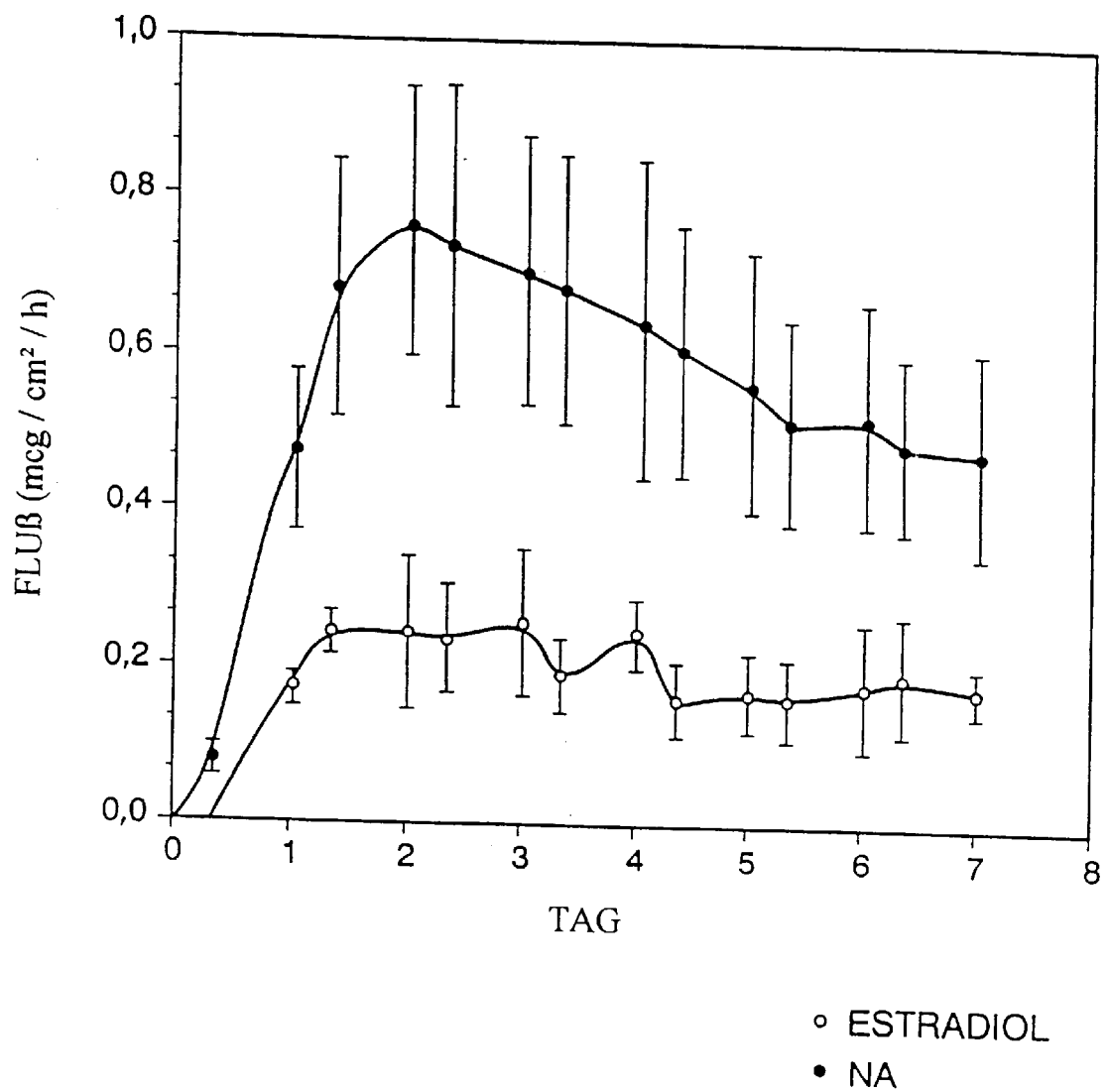
FIG. 3 is a graph illustrating the fluxes attainable in drug delivery systems employing the present invention.

In vitro Franz flow-through cells were used to determine the penetration of mixtures of norethindrone acetate and estradiol in an acrylate matrix system. The system was similar to Example 3. The drug reservoir layer was made with 2% estradiol, 10% norethindrone acetate and 20% PVP (BASF, K-30) in Morstik acrylate pressure-sensitive adhesive (#607). The backing layer contained an occlusive PIB layer and an elastomeric layer (Bertek 810). The in vitro skin fluxes for both drugs during a 7 day period are presented in FIG. 3. This figure shows that the flux of both drugs reached steady state within 24 hours and then maintained at steady state for the rest of the seven day permeation study. The average flux for estradiol was 0.21±0.06 (mcg/cm$^2$/hr) while the average flux for norethindrone acetate was 0.62±0.16 (mcg/cm$^2$/hr). These values suggest that sufficient amounts of estradiol and norethindrone acetate can be delivered without incorporation of an enhancer.

EXAMPLES 5–8

The experiments of Example 4 are repeated making changes in the composition of the reservoir:

In Example 5, the Morstik 607 is replaced with Monsanto GELVA® 737.

In Example 6, the Morstik 607 is replaced with a 4:1 mixture of GELVA® 737:GELVA® 788.

In Example 7, the Morstik 607 is replaced with a 9:1 mixture of GELVA® 737:GELVA® 788.

In Example 8, the PVP is replaced with similar levels of polyvinylalcohol.

In each case favorable results similar to those seen in example 4 are attained.

What is claimed is:

1. A drug-containing matrix for use in a transdermal drug delivery device for administering at least one estrogen to an area of skin or mucosa comprising the estrogen dispersed in a body of a pressure sensitive adhesive, said pressure-sensitive adhesive comprising an acetate acrylate copolymer and polyvinylpyrrolidone, said matrix being essentially free of a skin permeation enhancer.

2. The matrix of claim 1, wherein the estrogen is dispersed in the pressure sensitive adhesive in an amount at or below saturation.

3. The matrix of claim 1, wherein the acrylate copolymer comprises 2-ethylhexyl acrylate.

4. The matrix of claim 1, wherein the copolymer comprises at least one comonomer selected from the group consisting of vinyl acetate, acrylic acid and methyl acrylate.

5. The matrix of claim 4, wherein the copolymer comprises 2-ethylhexyl acrylate and vinyl acetate.

6. The matrix of claim 5, wherein the copolymer comprises approximately 72 wt % 2-ethylhexyl acrylate and approximately 28 wt % vinyl acetate.

7. The matrix of claim 3, wherein the copolymer comprises approximately 70 wt % 2-ethylhexyl acrylate and approximately 28 wt % vinyl acetate.

8. The matrix of claim 3, wherein the copolymer comprises approximately 85 wt % 2-ethylhexyl acrylate and approximately 10 wt % methyl acrylate, approximately 3 wt % acrylic acid and approximately 2 wt % vinyl acetate.

9. The matrix of claim 1, wherein the estrogen is selected from the group consisting of estradiol, ethinyl estradiol, esters of estradiol or a combination thereof.

10. The matrix of claim 1, further comprising a progestogen.

11. The matrix of claim 9 or 10, wherein the estrogen is estradiol.

12. The matrix of claim 9, wherein the estradiol ester is selected from the group consisting of estradiol valerate, estradiol cyprionate, estradiol decanoate and estradiol acetate.

13. The matrix of claim 11, wherein the progestogen is selected from the group consisting of norethindrone, norethindrone acetate, desogestrel, 3-keto desogestrel, gestadene and levonorgestrel.

14. The matrix of claim 13, wherein the progestogen is norethindrone acetate.

15. The matrix of claim 1, wherein the estrogen is estradiol.

16. The matrix of claim 10, wherein the estrogen is estradiol and the progestogen is norethindrone acetate.

17. The matrix of claim 1, wherein the copolymer comprises approximately 70 wt % 2-ethylhexyl acrylate and approximately 28 wt % vinyl acetate and the estrogen is estradiol.

18. The matrix of claim 10, wherein the copolymer comprises approximately 70 wt % 2-ethylhexyl acrylate and approximately 28 wt % vinyl acetate, the estrogen is estradiol and the progestogen is norethindrone acetate.

19. A transdermal or transmucosal drug delivery device for administering at least one steroid drug to an area of skin or mucosa comprising:
   (a) a layer of backing material which is substantially impermeable to the drug and laminated thereto; and
   (b) an adhesive drug-containing matrix as defined in any of claims 1, 10, 17 or 18.

20. A method for delivering a estrogen comprising applying the matrix of the device of claim 19 to the skin or mucosa of said patient.

* * * * *